United States Patent
Huntley, Jr.

(10) Patent No.: US 11,565,980 B2
(45) Date of Patent: Jan. 31, 2023

(54) SYSTEM AND METHOD FOR ORGANICALLY ENHANCING PLANT GROWTH

(71) Applicant: Coleman Scott Huntley, Jr., Austin, TX (US)

(72) Inventor: Coleman Scott Huntley, Jr., Austin, TX (US)

( * ) Notice: Subject to any disclaimer, the term of this patent is extended or adjusted under 35 U.S.C. 154(b) by 0 days.

(21) Appl. No.: 17/218,150

(22) Filed: Mar. 30, 2021

(65) Prior Publication Data

US 2021/0253489 A1    Aug. 19, 2021

Related U.S. Application Data

(60) Continuation-in-part of application No. 16/682,102, filed on Nov. 13, 2019, now abandoned, which is a (Continued)

(51) Int. Cl.
| | |
|---|---|
| *C12M 3/00* | (2006.01) |
| *C05F 17/00* | (2020.01) |
| *C05F 17/914* | (2020.01) |
| *A01N 63/00* | (2020.01) |
| *C12N 1/20* | (2006.01) |

(Continued)

(52) U.S. Cl.
CPC ............ *C05F 17/914* (2020.01); *A01C 21/00* (2013.01); *A01C 23/042* (2013.01); *A01N 63/00* (2013.01); *C05F 11/08* (2013.01); *C05F 17/20* (2020.01); *C05F 17/979* (2020.01); *C05F 17/986* (2020.01); *C12N 1/20* (2013.01); *Y02P 20/145* (2015.11); *Y02W 30/40* (2015.05)

(58) Field of Classification Search
CPC ............ C05F 17/0211; C05F 17/0036; C05F 17/027; C05F 17/0276; C05F 11/08; A01N 63/00; C12N 1/20; A01C 21/00; A01C 23/042; Y02P 20/145; Y02W 30/43
See application file for complete search history.

(56) References Cited

U.S. PATENT DOCUMENTS

| | | | |
|---|---|---|---|
| 3,865,126 A * | 2/1975 | Baggaley | F04B 9/107 137/99 |
| 4,635,848 A * | 1/1987 | Little | A01C 23/042 239/323 |

(Continued)

*Primary Examiner* — Nathan A Bowers
(74) *Attorney, Agent, or Firm* — Alford Law Group, Inc.; Vy H. Vu; William E. Alford

(57) ABSTRACT

A mobile, self-contained system for enhancing plant growth comprising: a mobile structure comprising a plurality of wheels so that the system can be moved; a vessel supported by the structure; a recirculating pump supported by the structure and exterior to the vessel, the pump having a first discharge line and a second discharge line; a generator supported by the structure; a vessel outlet from a bottom portion of the vessel to the pump; and an aerator for injecting air into the first discharge line; wherein the first discharge line extends from the pump directly into the bottom portion of the vessel, such that the contents of the vessel can be recirculated by the pump from the vessel outlet back into the (Continued)

vessel through the first discharge line and the second discharge line extends from the pump and is adapted for discharging contents of the vessel directly into an irrigation system.

19 Claims, 4 Drawing Sheets

Related U.S. Application Data continuation of application No. 16/184,672, filed on Nov. 8, 2018, now Pat. No. 10,479,736, which is a division of application No. 15/522,283, filed as application No. PCT/US2015/057646 on Oct. 27, 2015, now abandoned.

(60) Provisional application No. 62/069,068, filed on Oct. 27, 2014.

(51) Int. Cl.
*A01C 21/00* (2006.01)
*A01C 23/04* (2006.01)
*C05F 11/08* (2006.01)
*C05F 17/20* (2020.01)
*C05F 17/979* (2020.01)
*C05F 17/986* (2020.01)

(56) References Cited

U.S. PATENT DOCUMENTS

| | | | | |
|---|---|---|---|---|
| 5,135,174 A * | 8/1992 | Chaplinsky | ........... | B05B 12/085 239/310 |
| 5,447,866 A * | 9/1995 | Runyon | .................... | B09C 1/10 210/610 |
| 5,833,857 A * | 11/1998 | Roth | ....................... | C02F 3/121 210/610 |
| 6,148,839 A * | 11/2000 | Gonske | ................ | G05D 11/132 137/9 |
| 6,979,116 B2 * | 12/2005 | Cecala et al. | ....... | B01F 35/8311 366/132 |
| 8,210,451 B1 * | 7/2012 | Gooch et al. | ........ | A01C 23/042 137/268 |
| 8,297,535 B1 * | 10/2012 | Reid | .................... | A01C 23/042 239/316 |
| 9,121,012 B2 * | 9/2015 | Scott et al. | ............. | C12M 21/02 |
| 2007/0205225 A1 * | 9/2007 | Bomze | .................... | F04B 9/107 222/334 |
| 2007/0215722 A1 * | 9/2007 | Smith, III et al. | ... | A01C 23/042 239/398 |
| 2007/0220808 A1 * | 9/2007 | Kaprielian et al. | .. | A01G 27/003 47/48.5 |
| 2009/0255180 A1 * | 10/2009 | Felknor et al. | ....... | A01C 23/042 47/62 N |
| 2010/0176218 A1 * | 7/2010 | Carpenter | ............ | A01C 23/042 239/310 |

\* cited by examiner

SYSTEM AND METHOD FOR ORGANICALLY ENHANCING PLANT GROWTH

CROSS-REFERENCE TO RELATED APPLICATION

This United States (U.S.) patent application is a continuation-in-part and claims priority to U.S. patent application Ser. No. 16/682,102, titled "SYSTEM FOR ENHANCING PLANT GROWTH, filed on Nov. 13, 2019, now abandoned. Application Ser. No. 16/682,102 is a continuation of Ser. No. 16/184,672, titled "A Method for Improving Plant Growth by Irrigation with Nutrients," filed Nov. 8, 2018 by inventor Coleman Scott Huntley, Jr., now issued as U.S. Patent No. 10,479,736. Application Ser. No. 16/184,672 claims priority to and is a divisional application of U.S. Non-Provisional patent application Ser. No. 15/522,283, titled "A System for Enhancing Plant Growth," filed Apr. 26, 2017 by inventor Coleman Scott Huntley, Jr., now abandoned. Application Ser. No. 15/522,283 claims priority to and is a national stage patent application of International Patent Application No. PCT/US2015/57646, titled "A System for Enhancing Plant Growth," filed Oct. 27, 2015 by inventor Coleman Scott Huntley, Jr. Application No. PCT/US2015/057646 claims the benefit of U.S. Provisional Patent Application No. 62/069,068 titled "Microorganism Brew System," filed Oct. 27, 2014 by inventor Coleman Scott Huntley, Jr., the contents of which are incorporated in this disclosure by reference in their entirety."

BACKGROUND

There is a need for organic, safe, inexpensive, natural aids for growing plants. Furthermore, there is a need for a single system that can deliver both organic and inorganic nutrients to plants and soil. Natural aids that contain beneficial microorganisms help prevent root and foliar diseases as well as adding nutrients to plants and soil. Such organic aids are becoming more recognized in commercial agriculture as a healthier alternative to pesticides and fertilizers. There is a further need to precisely dilute, mix and deliver nutrient enhanced irrigation water evenly to all plants in a field during regular irrigation cycles in a timely manner.

Attempts to meet some of these needs are described in U.S. patent application Ser. Nos. 10/024,854, 09/847,893, and 11/224,554 and U.S. Pat. No. 7,972,839. However, each of these attempts has deficiencies such as being bulky, expensive, immobile, and excessively complex.

Therefore, there is a need for a system that overcomes the disadvantages of the existing systems.

SUMMARY

The embodiments of the invention are summarized by the claims that follow below.

DRAWINGS

These and other features, aspects and advantages of the present invention will become better understood with regard to the following description, appended claims, and accompanying figures where:

DETAILED DESCRIPTION

Figure 1:
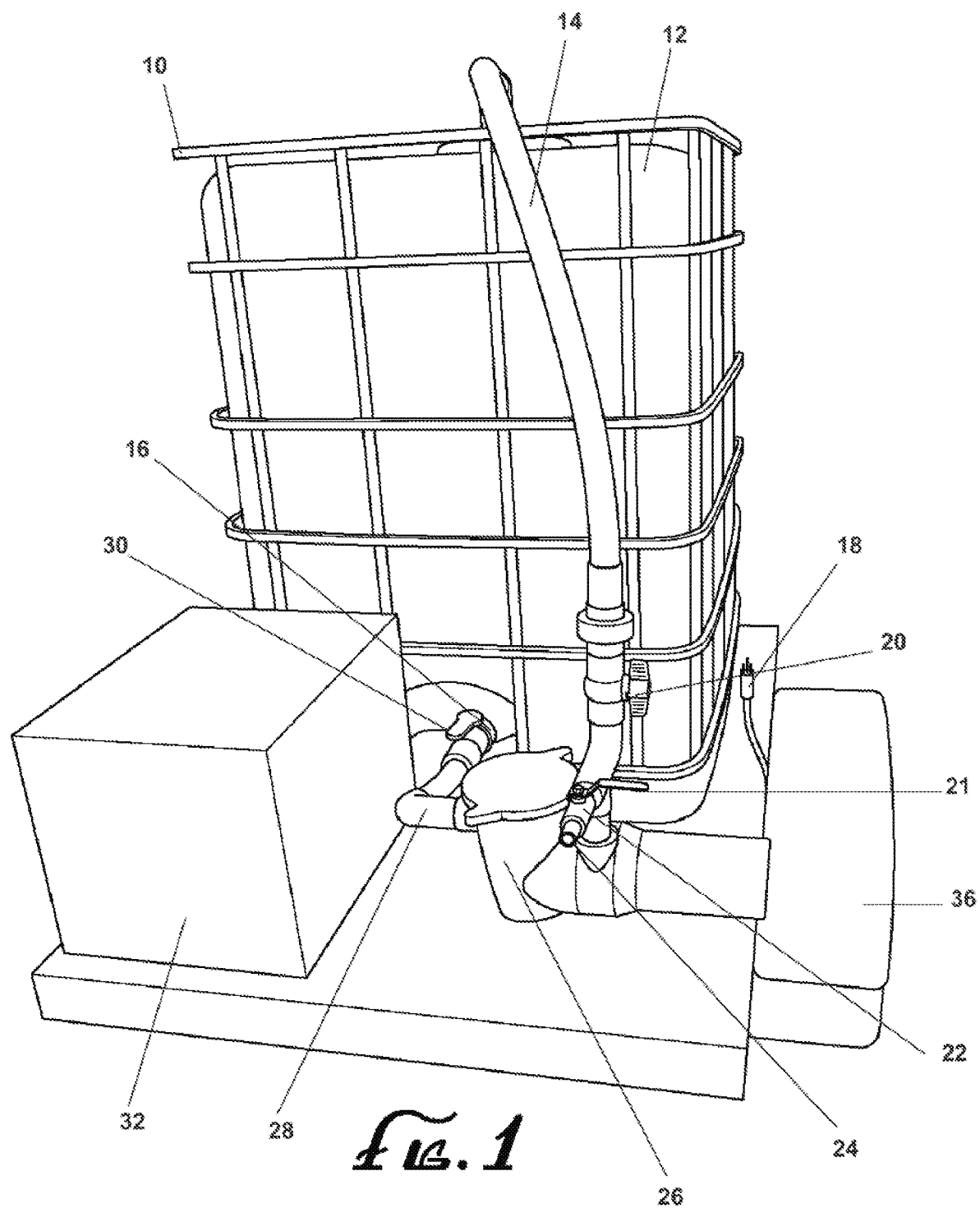
FIG. 1 is a front perspective view of a system having features of the present invention.

The present disclosure is directed to a system mobile and self-contained system for organically enhancing plant growth that satisfies the need for a precisely controllable fertigation system. The system is designed for both growing aerobic and anaerobic microorganisms and administering the microorganisms to plants to enhance plant growth. The microorganisms are an organic biofertilizer that can fix nutrients such as nitrogen and phosphate to the plants thus enhancing their growth. The system and method provide a mobile brewery that is simple and efficient and can easily be administered to plants via an irrigation system. Furthermore, this system utilizes an aerator to maintain a high level of dissolved oxygen continuously throughout the system.

To be sold or labeled as '100 percent organic,' "organic," or "made with organic (specified ingredients or food group(s)," the product must be produced and handled without the use of . . . sewage sludge. "4-National Organic Standards Board Certification, USDA"[1] Embodiments of the invention are "organic" per USDA definition as the components and selected microbes and microbial growth medial are produced and handled without the use of sewage sludge.

[1] USDA regulation for organic Irrigation § 205.105.

In particular, the device comprises a mobile structure having a plurality of wheels so that the system can be moved to an irrigation system; a vessel supported by the structure for receiving water and nutrients, wherein the vessel can contain from 200 up to 600 gallons of water; a diaphragm pump supported by the structure and exterior to the vessel, the pump having a first discharge line and a second discharge liner; a generator supported by the structure for powering the pump; a vessel outlet from a bottom portion of the vessel to the pump; and an aerator for injecting air into the first discharge line for aerating the contents of the vessel. Furthermore, the aerator can be a venturi. The aerator can be removable to allow circulation of nutrients, such as inorganic nutrients, that do not require oxygen rich environments.

Previously, this disclosure discussed nutrients to promote microbial growth. Hereinafter these nutrients that promote microbial growth will be called microbial growth media to differentiate them from plant growth nutrients.

Plant growth nutrients are the nutrients that are added to the soil to organically enhance plant growth. Plant growth nutrients are added to the soil by the microbes brewed in the system and method disclosed in this application. Biofertilizer, such as the microbes used in Applicant's disclosure, enhance plant growth by fixing nutrients such as nitrogen and phosphate. They add usable nutrients to the plants and soil to enhance plant growth.

Generally, a power source is included in the system needed to power the pump. Optionally, instead of a generator, the system can be provided with a power cord for providing AC power to the pump. Whether a generator or AC power is used depends on the size of the system and where the system is to be deployed. It is within the scope of the disclosure for the pump to use any reasonable means of power or power source, including but not limited to solar, wind, geo-thermal, hydroelectric or even powering the pump directly using a water powered pump.

The aerator can be disposed external and above the vessel for continuously aerating the solution as it is pumped through the aerator and back into the vessel. Furthermore, the first discharge line can comprise a first section from the pump to the top of the vessel and a second down section extending from the first section to the bottom portion of the vessel. Optionally, the second discharge line can be removed easily with a wrench, screw, or by hand. This allows changing out the second discharge line for injection into different pre-existing irrigation systems. For anaerobic microorganisms, optionally the aerator can be removable to allow use with microorganisms and microbial growth media that do not require oxygen.

The first discharge line extends from the pump to the bottom portion of the vessel such that the contents of the vessel can be recirculated by the pump from the vessel outlet back into the vessel through the first discharge line. The second discharge line extends from the pump and is adapted for discharging contents of the vessel directly into an irrigation system for plants.

In order to control the flow rate and direction of the solution each discharge line can have a valve for selecting where and at what flow rate the pumped contents of the vessel are discharged. Thus, the user can easily alternate the flow of the solution from continuous circulation to discharging onto plants. The user can also determine the flow rate of the discharge into an irrigation system by adjusting the aperture size of the valve and speed of the pump.

The disclosure also includes a method for growing microorganisms and circulating microbial growth media for administering to plants. The method comprises the steps of adding water, microorganisms, and microbial growth media into the vessel; circulating the contents with the pump by withdrawing contents of the vessel from the vessel outlet back into the vessel through the first discharge line, wherein air is sucked into the first discharge line by the venturi for aerating the contents of the vessel; cease pumping the contents of the vessel through the first discharge line; and pumping contents of the vessel with the pump out of the vessel through the second discharge line into an irrigation system for enhancing the growth of plants. Another method requires that the aerator be removed before cycling the contents of the vessel. Optionally, the system can further comprise a valve in the vessel outlet, and optionally, the top of the vessel is open to the atmosphere. The vessel can be modular so that the vessel can be separated from the other components of the system for cleaning.

Optionally, the user can move the vessel before pumping the contents out of the vessel. Furthermore, the user can optionally choose to attach the second discharge line to an irrigation system or a spray before pumping the contents of the vessel out. After discharging the contents of the vessel, the user can disconnect the vessel entirely from all other component parts for effective cleaning.

Fertigation is a method of plant fertilization in which liquid fertilizer is added to the water in an irrigation system. This is frequently referred to as precision agriculture and is known to reduce soil erosion and water consumption and reduces the amount of fertilizer utilized when the time, duration and injection rate are precisely controlled.

Over the last few decades, many new, innovative technologies have been developed for precision farming. Some of these are satellite positioning (GPS) systems, automated steering systems, remote sensing, geo-mapping and variable rate technology. Precision agriculture, satellite farming or site-specific crop management is a farming management concept based on observing, measuring and responding to inter and intra-field variability in crops. Fertigation can be a precision agriculture technique only if it can be measured and distributed accurately. If fertilizer is not diluted precisely there is danger of foliage burn. If the application in the field is not consistent throughout the entire field, then crop yields suffer.

The disclosed embodiments accurately and evenly distribute mixed soil amendments precisely at specific times, durations and intervals.

With reference to the figures, there is a system having features of the present invention comprising a mobile structure 36. The structure 36 can be towable or self-propelled. The structure supports the entire system including a vessel 12, a generator 32, a pump 26, piping, and a venturi 34 serving as an aerator. An exemplary embodiment of the mobile structure 36 can be approximately 4 feet wide and 6 feet long. Preferably, the mobile structure 36 is approved for use on state and federal highways with a load limit of 3,200 pounds. The size of the mobile structure 36 was determined by the need to be small enough to navigate through fields and orchards and low enough to the ground to enable one person to load or offload an empty tank.

Herein, the term "line" can refer to any structure capable of transporting a liquid, for example this could include a pipe. The term "pipe" is not meant to be exclusive but an example of one such "line" and can include other structures capable of transporting a liquid. The term "aerator" can comprise any structure capable of introducing air into the system; a venturi is one type of aerator.

Figure 3:
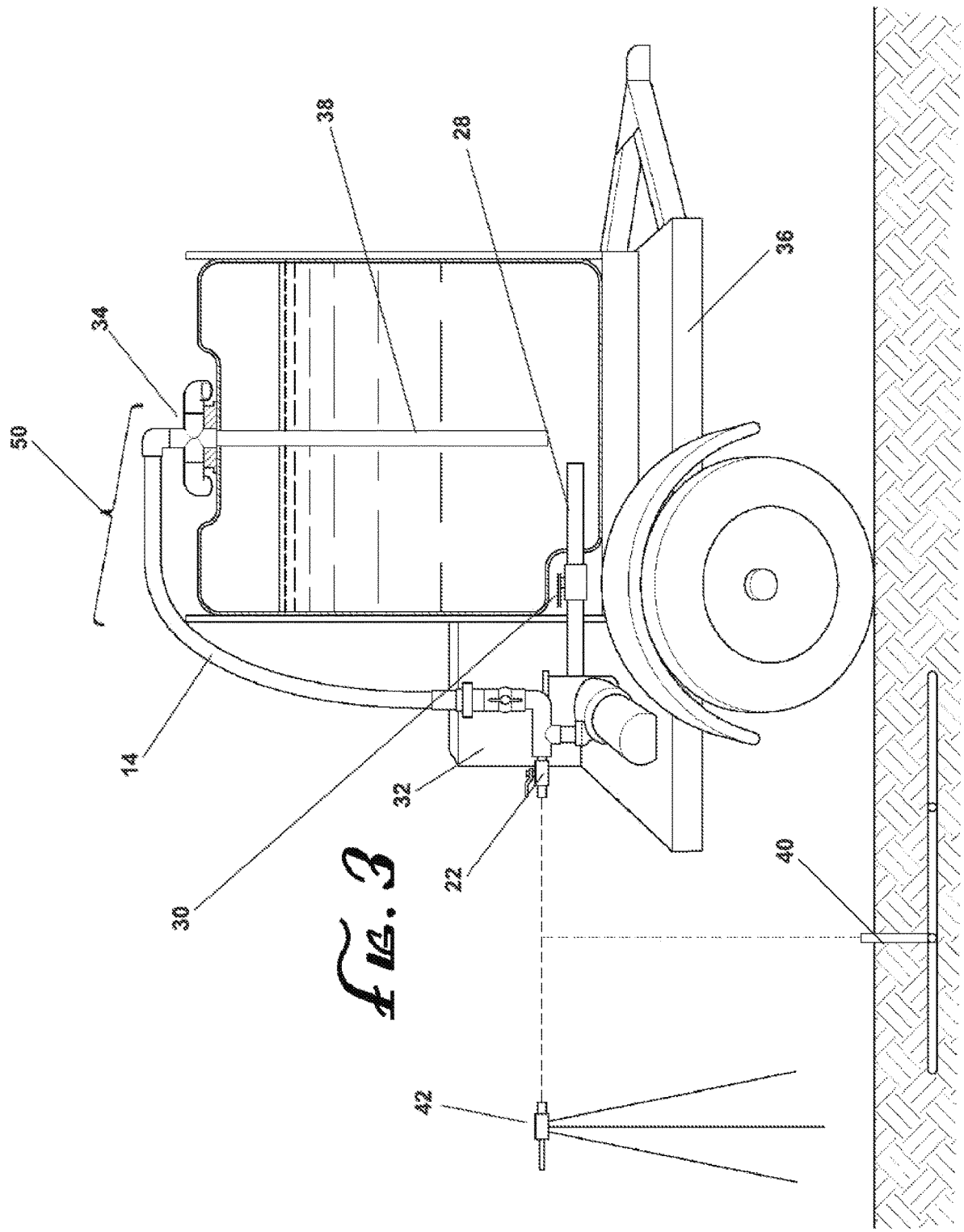
FIG. 3 is a side view of the system of FIG. 1, partially in section.

Referring to FIGS. 1 and 3, the system provides for continual circulation and aeration of a microorganism solution. A mixture of microorganisms, microbial growth media, and water are contained within the vessel 12. Vessel 12 can be any tank of appropriate size and material to hold liquid fertilizer. In some embodiment, the vessel 12 is a common shipping and distribution tote. This container is preferred because the tote is commonly the container in which fertilizers are shipped to the site by rail or truck.

The pump 26 extracts from the bottom of the vessel 12 the solution through a vessel outlet opening 16 and a vessel outlet pipe 28. A first discharge line 50 circulates the vessel contents. The first discharge line 50 can comprise a first section 14 from the pump to the top of the vessel and a second down section 38 extending from the first section 14 to the bottom portion of the vessel 12. The pump forces the solution up the first section 14 of the first discharge line 50 to a venturi 34 or aerator 34. As the solution passes through the venturi 34, the solution is aerated and forced back down into the vessel 12 via the second section 38 of the first discharge line 50. The system continues this circulation for the entire cultivation time until the solution is ready for application. This ensures continuous oxygen saturation and high quality and concentration of beneficial microorganisms. However, if the solution does not need to be aerated during the brewing or mixing process, the venturi 34 can be removed and the solution circulated with no aeration.

Referring to FIGS. 1 and 3, the system is designed for mobile as well as stationary brewing and application. The entire system is supported by a mobile structure 36. The mobile structure 36 can be towable or self-propelled. There is a generator 32 for powering the pump 26 where an AC power is not readily available. The generator 32 allows for the system to be fully mobile and can be administered easily at any location. Optionally, the system comprises a power cord 18 to power the pump 26 when AC power is easily accessible. Any generator capable of powering such pump is envisioned. In one embodiment, the generator is a 4,000 watt portable PREDATOR™ generator.

Further, the system comprises a second discharge line 22 for administering the contents of the vessel. The second discharge line 22 can be connected to an irrigation system 40 or can be attached to a spray 42 for mobile applications of the solution.

In order to inject fertigation liquids into a pressurized water line the pounds per square inch (psi) of the injection line must be equal to or exceed the psi of the water line. In some embodiments, pump 26 can be a common irrigation pump, however precision agriculture requires that one controls and measure the exact amount of organic fertilizer being injected at the precise time within the irrigation cycle. By manipulating the psi of the pump, the injection rate can be calibrated relative to the psi of the water line and it is possible to measure the exact amount of fertigation liquids to be injected and for how long to achieve even distribution during the irrigation cycle, thus providing the ability to measure the injection. A diaphragm pump provides a means of injecting into the irrigation line at variable psi to calibrate the exact ratio of fertigation liquids being injected and for how long. This ability to precisely measure the application rate and duration of the injection are requirements of precision agriculture. Thus, preferably, the pump 26 is a diaphragm pump.

The system is designed for ease of access and ease of cleaning. An important aspect of brewing these high-quality aids is cleanliness of the equipment. "Harmful" microbes can live in biofilm. Biofilm is the substance that builds up in, and remains in a brewing machine if it is not thoroughly cleaned after each brew. If the machine is not clean for subsequent brews, then the "harmful" microbes that remain in the biofilm can reproduce exponentially along with the "good" microbes and negatively affect the quality of the organic aid produced. The vessel 12 is modular so the vessel can be separated from the other components of the system for cleaning. The entire vessel 12 can be removed from the system, as it is lightweight and detachable. Therefore, the invention is a system that is easy to use and easy to clean, and that is economical and simple to operate.

Referring to FIG. 3, the vessel 12 is contained within a holding crate 10. The holding crate 10 can be any material or configuration suitable for holding and supporting the vessel 12 stationary such as but not limited to a skeleton, bolts, or even recessed notches. The holding crate 10 is easily moved in the field and can be connected easily to provide any total volume of solution required to irrigate any size field. Furthermore, multiple holding crates 10 with the vessel 12 can be used as slaves in order to provide a larger volume of solution for a greater surface area to be applied. In this configuration multiple isolated units, each with its own pump and circulation system can be connected via piping or lines to one "master" second discharge line.

Figure 2:
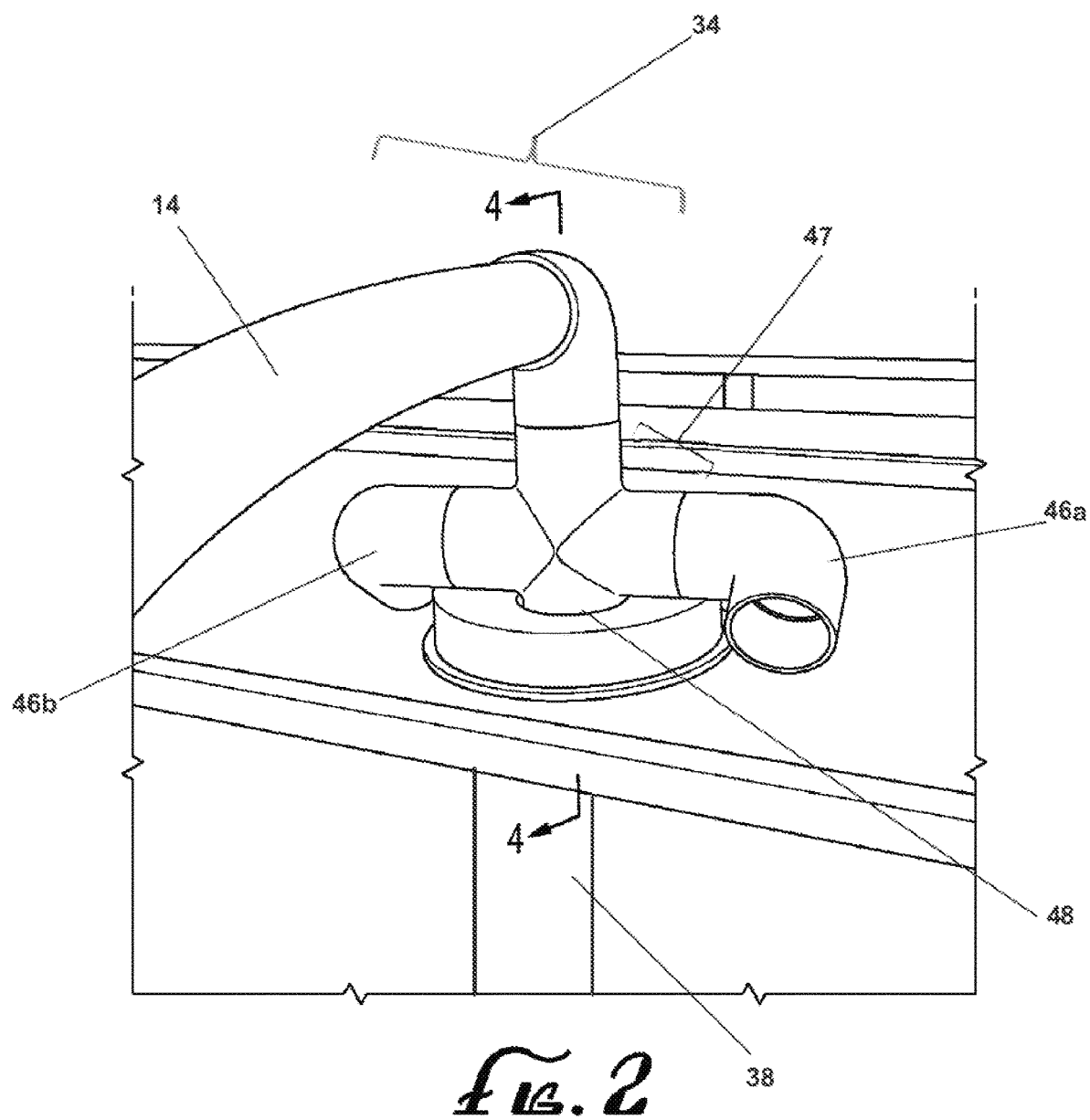
FIG. 2 is a perspective view of an aerating portion of the system of FIG. 1.

Only the vessel outlet pipe 28 and the second down section 38 of the first discharge line 50 are located interior to the vessel 12. However, both pipes can be easily removed and the vessel 12 completely removed for thorough cleaning. The pipes can be removed manually without tools or can require simple tools such as a screw and a wrench. Referring to FIG. 2, a "cross" 47 connects to the second down section 38 of the first discharge line 50 through an inlet 48 in the top of the vessel 12. Optionally a ball valve can be coupled to the venturi inlets 46a, 46b or to the down section 38 to regulate the amount of air passing into the system. Optionally, the "cross" 47 can be easily removed from the inlet 48 and the second down section of the first discharge line 50.

Preferably, the second down section 38 of the first discharge line 50 is connected permanently to the cross 47 but can be easily removed with the cross intact. The second down section 38 of the first discharge line 50 is easily removed from the inlet 48 and thus removed from the vessel 12 for cleaning. This simple design allows the user to efficiently clean the vessel 12 to eliminate any residual biofilm in the vessel 12. Optionally, the bottom opening of the second down section 38 of the first discharge line 50 can have diffusers.

Figure 4:
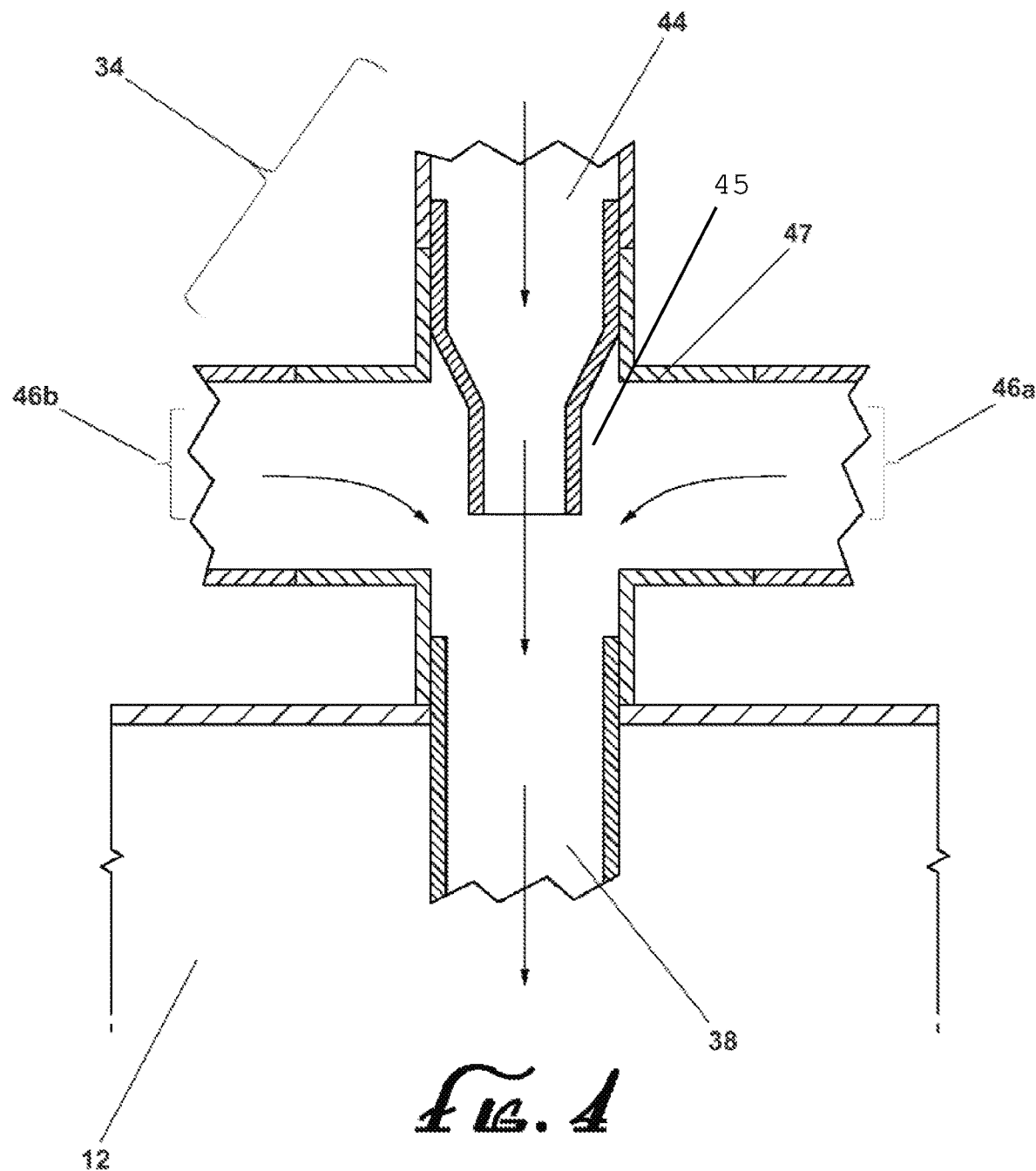
FIG. 4 is a sectional view of the aeration portion of the system of FIG. 1.

Referring to FIGS. 2 and 4, there is the venturi 34 that can provide optimum aeration of the liquid. Preferably, the venturi 34 maintains a continual minimum dissolved oxygen content of at least 6 ppm and typically up to 10 ppm. One configuration of an aerator, is the venturi 34. One configuration of the venturi 34 is comprised of the "cross" 47, two air/oxygen inlets 46a/b, a liquid inlet 45 and the descending second down section 38 of the first discharge line 50. The two oxygen inlets 46a/b are located opposite to each other and perpendicular to the flow of the liquid. Optionally, only one air inlet can be used. Liquid is pumped from the first section 14 of the first discharge line 50 to the top of the "cross" 47. As the liquid passes through the constricted pipe 44, creating a venturi effect, the two oxygen inlets 46a/b aerate the liquid. The aerated liquid is then pumped down the second down section 38 of the first discharge line 50 into the vessel 12. Furthermore, as seen in FIG. 3, the aerated liquid is forced down the second down section 38 of the first discharge line 50 to the bottom of the vessel 12 wherein the liquid "mushrooms" as it hits the flat surface of the bottom of the vessel and creates a swirling of the liquid similar to the motion of a washing machine. This process allows for uniform circulation throughout the vessel 12 as well as increasing the dissolved oxygen within the system.

The piping can be plastic or metal; the preferred piping is polyvinyl chloride.

It is desirable to control the flow rate and direction of the liquid. To accomplish this, the system comprises 4 or more or more valves: a vessel outlet valve 30 on the vessel outlet pipe 28 disposed between the pump 26 and the vessel 12, a first discharge valve 20 on the first section 14 of the first discharge line 50 disposed between the pump 26 and the "cross" 47, and a second discharge valve 21 on the second discharge line 22 disposed between the pump 26 and a barbed fitting 24 for attachment to an irrigation system. Using the valves, a user can alternate the direction and flow of the liquid from continuous circulation to the application on plants. For example, to maintain constant circulation, the pump 26 and generator 32 are turned on and first discharge valve 20 and vessel outlet valve 30 are opened while second discharge valve 21 is closed. Alternately, to discharge the contents of the vessel 12 while the pump 26 and generator 32 are on, second discharge valve 21 and vessel outlet valve 30 are opened while first discharge valve 20 is closed.

To further precisely control the flow rate and the psi of liquid into an irrigation system, the valves (20, 21, 30) are ball valves because when they are fully open, they offer no restrictions on the flow. This is done to preserve the integrity of the measuring process. Ball valves adjust to any flow and allow the precise measurement of the volume of water pumped into the irrigation lines by controlling the aperture size. Ball valves can incrementally increase or decrease flow rate in a system while the liquid is flowing, thus allowing the disclosed embodiments to adjust to the psi of the various irrigation systems that can be encountered in the field.

The water demand of the irrigation can vary during a typical irrigation cycle so it is desirable to measure the flow rate. This enables all of the water in the irrigation lines to be nutrient treated to assure even application of the nutrients to the medium. By varying the pressure output through the ball valve or from the second discharge line 22 and/or diameter of the discharge pipes, the system can be adapted to any irrigation system and will precisely measure the dilution rate of the solution in the irrigation system and the flow of irrigation water.

Furthermore, it is desirable to be able to accommodate different irrigation systems of which can have different size piping and maximum and minimum pressure loads. This can be accomplished by varying the pressure output of the pump 26, varying the degree that the second discharge valve 21 is opened or closed in the second discharge line 22, or by varying the diameter of the piping in the second discharge line 22. In order to account for the varying pressures needed in different irrigation systems, it is preferred to use a diaphragm pump for pumping the solution. A diaphragm pump, such as a double diaphragm pump, provides the benefits, among others, of pumping chambers preventing the material being pumped to come in contact with any close-fitting rotary or sliding seals to and capacities are infinitely variable within the pumps range. Because of the double diaphragm pump structure, it is ideal to be used with abrasives, slurries or even run dry. Therefore, there is no need to use variable speed motors or variable drives with a diaphragm pump.

Examples of the principles of the disclosed embodiments applied to precision agriculture is described at its most basic for ease of understanding. In one embodiment, one or more mobile systems of FIG. 1 are moved onto a field of crops or other cultivated plants. A standard irrigation system 40 supplies the field with water. One or more mobile systems of FIG. 1 are placed next to an input of the irrigation system 40. The second discharge line 22 can be connected to the irrigation system 40. The psi of the irrigation system 40 is known or can be measured by a psi gauge connected to the irrigation system 40. The diaphragm pump 26 used in embodiments of the invention, is selected to meet or preferably exceed the psi of the irrigation system.

After the second discharge line 22 is connected to the irrigation system 40, the diaphragm pump 26 can be controlled to pump faster, thus increasing the psi of the mobile system of FIG. 1 to meet or exceed the psi of the irrigation system 40. How much psi is needed depends on several factors that can be calculated before even placing the systems of FIG. 1 into the field and adjusted as needed during the fertigation process. The size of the field will determine the amount of organic fertilizer needed. The concentration of the fertilizer can be determined from the growth of the microorganisms during the cultivation time. Alternatively, the concentration of the liquid fertilizer can be known from using commercially available organic and inorganic fertilizer. Knowing the amount of fertilizer needed by the crops, the concentration of the microorganism, and the flow rate of the irrigation system, it is possible to calculate the dilution factor and adjust the diaphragm pump and discharge ball valve to achieve that dilution factor.

The diaphragm pump 26 and ball valve 21 can be operated manually to adjust to the fertigation needs of the plants being treated. Alternatively, these components may be controlled mechanically via automated solenoid valves or the like. The entire system can be placed on a timer to open and close the ball valves and run the diaphragm pump to precisely and regularly irrigate a field with the right amount of liquid fertilizer.

Another factor to consider is the irrigation cycle. For example, if the irrigation cycle is 1 hour, then the diaphragm pump can be adjusted to pump sufficient organic fertilizer from the vessel 12 into the irrigation system 40 in 1 hour. Pumping too slowly can result in organic fertilizer being left in the vessel 12 instead of being distributed by the irrigation cycle. Alternatively, pump too fast and a high concentration of organic fertilizer can result in foliage burn. One of the benefits of the embodiments of the disclosure is the ability to adjust the flow rate of the organic fertilizer being pumped into the irrigation system 40 ad hoc thus avoiding the too slow and too fast scenarios. The combination of diaphragm pump 26 and ball valve 21 allows fine adjustment of the flow rate of organic fertilizer pumped into the irrigation system 40.

Next, disclosed is the method of assembly of one embodiment of the invention. To create the venturi 34, take a 1.5 inch "bushing" and cut a "flange" off of the end (one quarter inch). Insert a 2.75 inch long 1 inch pvc pipe into the "bushing" so that it "seats" against the interior "flange" inside the "bushing" and hold in place in the center of the "cross" for one minute so that the glue dries. Insert the "bushing" into the "cross" 47 in the opposite direction that it was designed to be inserted so that the 2.75 inch long 1 inch pvc pipe extends into the center of the "cross" 47, leaving 0.5 inches of the (unglued) "bushing" outside the "cross" 47 so as to be accessible for inserting and gluing into a 1.5 inch "elbow". This leaves the 1 inch pvc pipe terminating in the middle of the "cross" 47 reducing the flow of liquid so as to create a venturi effect as the liquid passes through the "cross" 47 from top to bottom with the perpendicular "arms" of the cross serving as air inlets 46a/b. Using a conical boring device, bore out the top of the "bushing" where it enters the "cross" 47 and reduces to 1 inch to enhance the venturi effect of the cross 47. This is now the top of the system.

Next, use two 2 inch lengths of pipe as "sleeves" and glue the (2) "arms" of the cross 47 to the "elbows" so that the opening of the "elbows" points down at a 30 degree angle. Glue the third "elbow" to the top of the "cross" 47 so that it is perpendicular to the arms of the "cross" where the "bushing" extends out 0.5 inch (over the venturi 34). Glue a 50 inch flexible pipe into the bottom arm of the "cross". This is now the second down section of the first discharge line 50 that inserts into the tank. Glue the flexible pipe into the "elbow" above the venturi. This is now the first discharge pipe 14. Glue the end of the flexible pvc pipe to the "union". This "union" will connect the flexible pipe to the valve 20 coming out of the pump.

Furthermore, the invention relates to a method for growing microorganisms and administering the microorganisms for enhancing the growth of plants using the systems of the invention. The method comprises adding water, microorganisms, and microbial growth media for the microorganisms into the vessel 12. Pumping to aerate the vessel 12 for a sufficient time to allow a majority of the microorganism to grow and develop. The contents of the vessel are circulated through the first section 14 of the first discharge line 50 to the liquid inlet 45, wherein air is sucked into the first discharge pipe 50 for aerating the contents of the vessel. Next, pump contents of the vessel 12 with the pump 26 out of the vessel for enhancing the growth of plants. The time required to circulate the contents of the vessel depends on the amount of solution and the area necessary to be irrigated in order to allow a majority of the microorganisms to fully develop.

Alternatively, microorganisms and microbial growth media can be circulated for administering to plants wherein the aerator 34 is removed before pumping to allow circulation without the introduction for air into the system. Alternatively, ball valves coupled to the aerator 34 can be closed instead of removing the aerator 34.

In the preferred embodiment of the invention the capacity to brew is up to 500 gallons of solution, because the readily availed totes have a 500 gallon capacity. However, the brew capacity should not be considered a limitation of the disclosure, as the disclosed embodiments can be scaled to any size operation, from the smallest residential backyard to the largest commercial field. Depending on the bacteria desired and cultivation time, in one embodiment brewing generally takes up to 24 hours. However, it is envisioned that less brewing time can be required. Preferably, the system is transported to the site of application and then brewed on site; however, brewing can take place anywhere as the system is mobile.

Optionally, the user can move the vessel 12 before pumping the contents out of the vessel 12. Furthermore, the user can optionally choose to attach the second discharge pipe 22 to an irrigation system 40 or a spray 42 before pumping the contents of the vessel. After discharging the contents of the vessel 12, the user can disconnect the vessel entirely from all other component parts for effective cleaning.

The microorganisms can comprise aerobic microbes consisting of archaea, bacteria, fungal hyphae, flagellates, amoebae, some ciliates, yeast cells and yeast fungal hyphae. The microbial growth media solution can be composed of any appropriate nutrients for such microorganisms, for example but not limited to black strap molasses, fish hydrolysate, and kelp meal. A product containing both microorganisms and microbial growth media is available from Simple Science LLC located in Salt Lake City, Utah, under the mark DIRT2SOIL. The microbes disclosed are selected to add or fix plant growth nutrients to the plant and soil, thereby organically enhancing plant growth. The microbial growth media solution promotes microbial propagation when brewed in embodiments of the disclosure.

Beneficial microorganisms help prevent root and foliar diseases as well as adding nutrients to plants and soil. Such organic aids are becoming more recognized in commercial agriculture as a healthier alternative to pesticides and fertilizers.

Although the present invention has been described in considerable detail with reference to certain preferred versions thereof, other versions are possible. For example, different aerating means may be employed such as an air pump. Likewise, microbial fertilizers are the preferred means of enhancing plant growth and the detailed description focuses mainly on the system and method of distributing microbial fertilizer to enhance plant growth. However, it has been found that the system of FIG. 1, can be used, and is extremely well adapted, to distributing any type of plant growth enhancing fertilizer available. The system of FIG. 1 is adapted to mix and precisely distribute powder, liquid, crystal fertilizer in controlled concentration to enhance plant growth. Therefore, the spirit and scope of the appended claims should not be limited to the description of the preferred versions contained herein.

The invention claimed is:

1. A mobile, self-contained system for enhancing plant growth comprising:
   a. a mobile structure comprising a plurality of wheels so that the system can be moved to an irrigation system;
   b. a vessel supported by the structure for receiving water, microbes adapted to add nutrients to organically enhance plant growth, and microorganism growth media, wherein the vessel can contain up to 600 gallons of water;
   c. a pump supported by the structure and exterior to the vessel, the pump having a first discharge line and a second discharge line;
   d. a generator supported by the structure for powering the pump;
   e. a vessel outlet from a bottom portion of the vessel to the pump; and
   f. an aerator for injecting air into the first discharge line for aerating the contents of the vessel supported by the structure
      wherein the first discharge line extends from the pump into the bottom portion of the vessel, such that the contents of the vessel can be recirculated by the pump from the vessel outlet back into the vessel through the first discharge line, and
      wherein the second discharge line extends from the pump and is adapted for discharging contents of the vessel directly into an irrigation system for plants,
      wherein each discharge line has a valve, used separately or in conjunction with the pump, to comprise a flow controller configured for controlling the flow rate of the discharged contents into the irrigation system.

2. The system of claim 1, wherein the microorganism growth media comprise inorganic microbial growth nutrients.

3. The system of claim 1, wherein the aerator is removable.

4. The system of claim 1, wherein the aerator comprises a venturi.

5. The system of claim 1, wherein the aerator comprises two air inlets into the first discharge line.

6. The system of claim 1, wherein the aerator is disposed exterior to the vessel and above a top of the vessel.

7. The system of claim 1, wherein the valve is a ball valve and the pump is diaphragm pump.

8. The system of claim 1, further comprising a valve in the vessel outlet.

9. The system of claim 1, wherein a top of the vessel is open to the atmosphere.

10. The system of claim 1, wherein the vessel is modular so the vessel can be separated from the other components of the system for cleaning.

11. A mobile, self-contained system for enhancing plant growth comprising:
   a. a mobile structure comprising a plurality of wheels so that the system can be moved to an irrigation system;
   b. a vessel supported by the structure for receiving water, microbes adapted to add nutrients to organically enhance plant growth, and microorganism growth media;
   c. a recirculating pump supported by the structure and exterior to the vessel, the pump having a first discharge line and a second discharge line;
   d. a generator supported by the structure for powering the pump;
   e. a vessel outlet from a bottom portion of the vessel to the pump; and
   f. an aerator for injecting air into the first discharge line for aerating the contents of the vessel supported by the structure;

wherein the first discharge line extends from the pump into the bottom portion of the vessel, such that the contents of the vessel can be recirculated by the pump from the vessel outlet back into the vessel through the first discharge line, and wherein the second discharge line extends from the pump and is adapted for discharging contents of the vessel directly into an irrigation system for plants, wherein each discharge line has a valve, used separately or in conjunction with the pump, to comprise a flow controller configured for controlling the flow rate of the discharged contents into the irrigation system.

12. The system of claim 11, wherein the microorganism growth media comprise inorganic microbial growth nutrients.

13. The system of claim 11, wherein the recirculating pump is a diaphragm pump.

14. The system of claim 11, wherein the vessel can contain from 250 to 500 gallons of water using standard totes.

15. The system of claim 11, wherein the aerator is disposed exterior to the vessel and above a top of the vessel.

16. The system of claim 11, wherein the valve is a ball valve.

17. The system of claim 11, wherein the vessel is modular so the vessel can be separated from the other components of the system for cleaning.

18. A method for growing microorganisms and circulating nutrients for administering to plants, the method comprising the steps of:
  a) selecting the system of claim 1;
  b) adding water, microorganisms, and microbial growth media into the vessel;
  c) circulating the contents with the pump by withdrawing contents of the vessel from the vessel outlet back into the vessel through the first discharge pipe, wherein air is sucked into the first discharge line and pumped to create a venturi for aerating the contents of the vessel;
  d) cease pumping the contents of the vessel through the first discharge line; and
  e) pumping contents of the vessel with the pump out of the vessel through the second discharge line for enhancing the growth of plants.

19. The method of claim 18, further comprising adjusting the pump and a ball valve coupled to the second discharge line to change a flow rate of contents of the vessel through the second discharge line to provide a calibrated amount of plant growth nutrient through an irrigation system coupled to the second discharge line.

* * * * *